United States Patent
Walt et al.

(10) Patent No.: US 9,664,667 B2
(45) Date of Patent: May 30, 2017

(54) DIGITAL QUANTIFICATION OF SINGLE MOLECULES

(71) Applicant: TUFTS UNIVERSITY, Medford, MA (US)

(72) Inventors: David R. Walt, Boston, MA (US); Manuel Alfredo Palacios, Stoneham, MA (US); Michael Lacy, West Chester, PA (US)

(73) Assignee: Trustees of Tufts College, Medford, MA (US)

( * ) Notice: Subject to any disclaimer, the term of this patent is extended or adjusted under 35 U.S.C. 154(b) by 384 days.

(21) Appl. No.: 14/390,164

(22) PCT Filed: Apr. 30, 2013

(86) PCT No.: PCT/US2013/038882
§ 371 (c)(1),
(2) Date: Oct. 2, 2014

(87) PCT Pub. No.: WO2013/166024
PCT Pub. Date: Nov. 7, 2013

(65) Prior Publication Data
US 2015/0112612 A1    Apr. 23, 2015

Related U.S. Application Data

(60) Provisional application No. 61/640,700, filed on Apr. 30, 2012.

(51) Int. Cl.
*C40B 30/10* (2006.01)
*G01N 33/48* (2006.01)
*G06F 19/24* (2011.01)
*G06F 19/10* (2011.01)

(52) U.S. Cl.
CPC ............ *G01N 33/48* (2013.01); *G06F 19/10* (2013.01); *G06F 19/24* (2013.01)

(58) Field of Classification Search
USPC ........ 506/9, 12; 205/777.5; 204/403.01, 406
See application file for complete search history.

(56) References Cited

U.S. PATENT DOCUMENTS

| | | | |
|---|---|---|---|
| 5,571,401 A * | 11/1996 | Lewis | G01N 27/126 204/406 |
| 5,916,539 A | 6/1999 | Pilgrimm | |
| 6,251,303 B1 | 6/2001 | Bawendi et al. | |
| 6,319,426 B1 | 11/2001 | Bawendi et al. | |
| 6,332,901 B1 | 12/2001 | Nagamiya et al. | |
| 6,350,369 B1 * | 2/2002 | Lewis | G01N 33/54373 204/403.01 |
| 6,423,551 B1 | 7/2002 | Weiss et al. | |

(Continued)

FOREIGN PATENT DOCUMENTS

| | | |
|---|---|---|
| RU | 2193797 C2 | 11/2002 |
| WO | WO-2011/059721 A1 | 5/2011 |

OTHER PUBLICATIONS

International Search Report for PCT/2013/038882, 2 pages (Aug. 22, 2013).

*Primary Examiner* — Lam Nguyen
(74) *Attorney, Agent, or Firm* — Choate, Hall & Stewart LLP

(57) ABSTRACT

The present disclosure, among other things, methods and systems for digital quantification of single molecule analytes.

3 Claims, 15 Drawing Sheets

(56) References Cited

U.S. PATENT DOCUMENTS

| | | |
|---|---|---|
| 6,426,513 B1 | 7/2002 | Bawendi et al. |
| 6,444,143 B2 | 9/2002 | Bawendi et al. |
| 6,576,291 B2 | 6/2003 | Bawendi et al. |
| 6,649,138 B2 | 11/2003 | Adams et al. |
| 6,815,064 B2 | 11/2004 | Treadway et al. |
| 2010/0317018 A1 | 12/2010 | Wohlgemuth |
| 2011/0054938 A1 | 3/2011 | Hood et al. |
| 2012/0202709 A1* | 8/2012 | Bergo .................. C40B 30/10 506/12 |

\* cited by examiner

DIGITAL QUANTIFICATION OF SINGLE MOLECULES

CROSS-REFERENCE TO RELATED APPLICATION

This application claims priority to and the benefit of, and incorporates herein by reference in its entirety, U.S. Provisional Patent Application No. 61/640,700, filed Apr. 30, 2012.

BACKGROUND

Detection and quantification of analytes is of fundamental importance in the fields of genetic and medical research, clinical chemistry, and forensic science, among others. Significant effort is invested in the development of new techniques, with a particular focus on improving sensitivity of detection and/or precision of quantification.

SUMMARY

The present invention provides methodologies for detecting single molecules by 1) providing, to a processor of a computing device, data representing level of signal detected at a first time point, $t_1$, from a plurality of locations on a substrate on which at least one single molecule analyte is detectable by virtue of being or being associated with at least one blinking agent, is located at a discrete position; 2) providing to the processor, data representing level of signal detected at at least one second time point, $t_2$, from the plurality of locations; 3) processing, by the processor, data sets from each location at each time point, so that a threshold for variation of the level of signal is determined using an algorithm; and 4) based on the determined threshold, establishing that locations with a positive count that reflects the presence of the single molecule analyte, whereas other locations do not contain a single molecule analyte and represent background signal.

The present invention, among other things, provides the insight that blinking behavior of a blinking agent can beneficially be employed to detect/quantify an analyte/event (e.g., change of an analyte). Blinking agents are typically known for causing trouble. For example, quantum dots have very similar brightness at a given period of time, but they can have very different integrated signal-to-noise ratios. According to the present disclosure, quantum dots and other blinking agents surprisingly can be utilized to improve detection/quantification of single molecules analytes.

Separately and additionally, the present invention provides the insight that variation of a signal of interest against the variations of background signal can be analyzed to obtain resulting data selected from the group consisting of sum, deviations (e.g., standard deviation), variance, and any combination thereof. Without being bound to any particular theory, the processing can improve the signal-to-noise ratio, such that it may enable detection and/or quantification of single molecule analytes.

Still further, the present invention also provides technologies to determine a threshold for resulting data using an algorithm. When resulting data are greater than the threshold, they represent positive counts and the locations of single molecule analytes are determined.

BRIEF DESCRIPTION OF THE DRAWING

The drawings are for illustration purposes only, not for limitation.

DEFINITIONS

Figure 1:
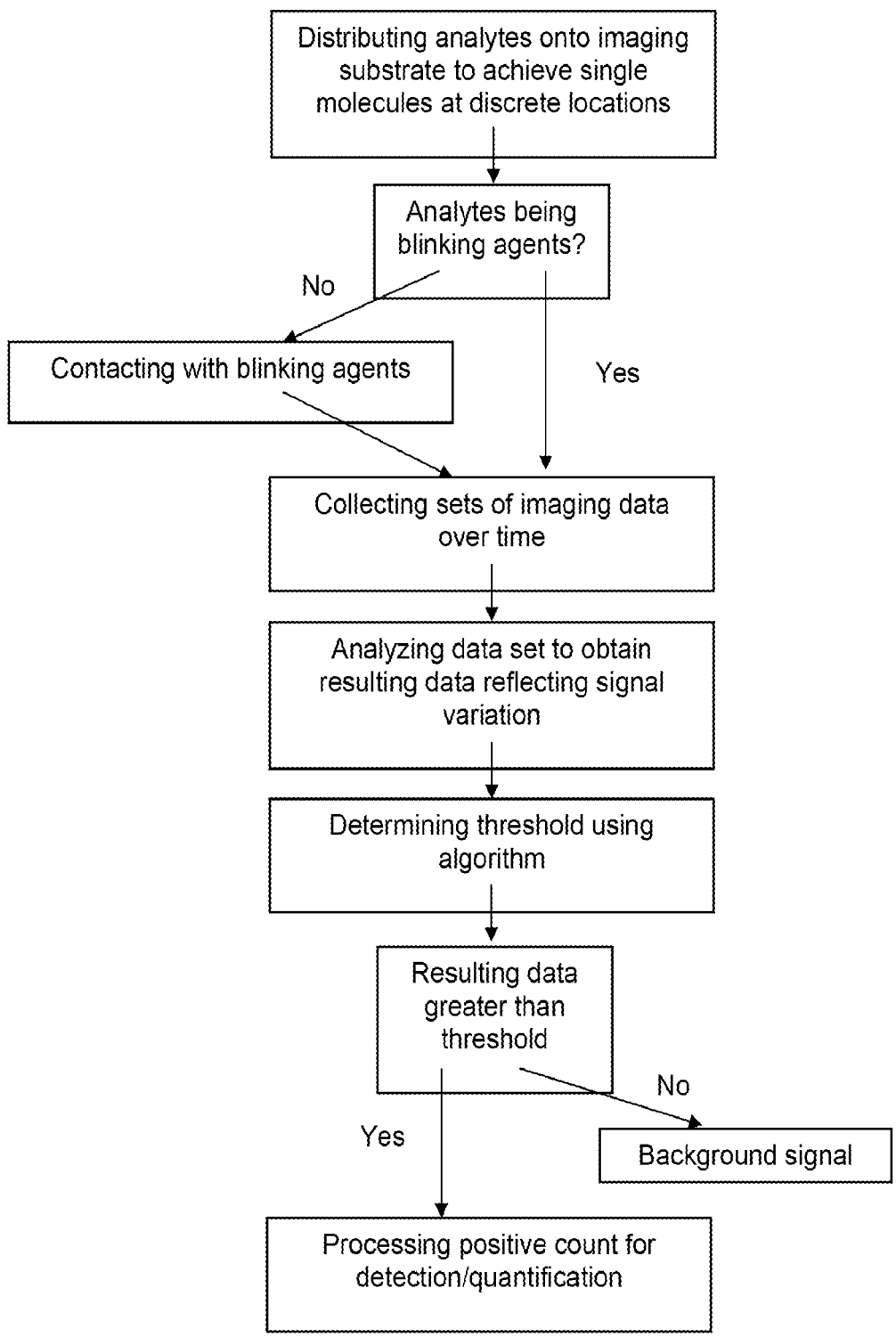
FIG. 1 illustrates an example flow chart of a data analysis process.

In order for the present invention to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "analyte" broadly refers to any substance to be analyzed, detected, measured, or quantified. Examples of analytes include, but are not limited to, proteins, peptides, hormones, haptens, antigens, antibodies, receptors, enzymes, nucleic acids, polysaccharides, chemicals, polymers, pathogens, toxins, organic drugs, inorganic drugs, cells, tissues, microorganisms, viruses, bacteria, fungi, algae, parasites, allergens, pollutants, and combinations thereof.

The term "associated" as used herein, typically refers to two or more moieties connected with one another, either directly or indirectly (e.g., via one or more additional moieties that serve as a linking agent), to form a structure that is sufficiently stable so that the moieties remain connected under the conditions in which the structure is used, e.g., physiological conditions. In some embodiments, associated moieties are attached to one another by one or more covalent bonds. In some embodiments, associated moieties are attached to one another by a mechanism that involves specific (but non-covalent) binding (e.g. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

A "blinking agent", as that term is used herein, is an entity characterized by a stochastic detectable feature (i.e., by a feature whose detectable attribute varies stochastically relative to a determined reference, e.g., time). In some embodiments, a detectable attribute varies stochastically due to Brownian motion. In some embodiments, the detectable feature is detectable optically. In some embodiments, a blinking agent is or comprises a particle.

The term "labeled" is used herein to describe a situation in which an entity (e.g., a nucleic acid probe, antibody, etc.) becomes detectable (e.g., visualizable), for example, by association with another entity (e.g., a nucleic acid, polypeptide, etc.) that comprises a detectable moiety. The detectable agent or moiety may be selected such that it generates a signal which can be measured. In some embodiments, a measurable feature (e.g., intensity) of the signal is related to the amount of a labeled entity. A wide variety of systems for labeling and/or detecting proteins and peptides are known in the art. Labeled proteins and peptides can be prepared by incorporation of, or conjugation to, a label that is detectable by spectroscopic, photochemical, biochemical, immunochemical, electrical, optical, chemical or other means. A label or labeling moiety may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Suitable detectable agents include, but are not limited to, radionucleotides, fluorophores, chemiluminescent agents, microparticles, enzymes (e.g., that catalyzes a reaction and generating one or more detectable entities), colorimetric labels, magnetic labels, haptens, molecular beacons, aptamer beacons, and the like.

The term "nucleic acid" as used herein, refers to a polymer of nucleotides. Deoxyribonucleic acids (DNA) or ribonucleic acids (RNA) and polymers thereof in either single- or double-stranded form are exemplary polynucleotides. Unless specifically limited, the term encompasses nucleic acid molecules containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. In some embodiments, a polynucleotide sequence of relatively shorter length (e.g., no more than 50 nucleotides, preferably no more than 30 nucleotides, and more preferably no more than 15-20 nucleotides) is typically referred to as an "oligonucleotide."

The term "particles" as used herein, refers to discrete objects. Such objects can be of any shape or size. In some embodiments, some or all particles are substantially spherical. In some embodiments, utilized particles have sized within a defined range and/or showing a defined distribution. In some embodiments, particles having a diameter of less than 1000 nanometers (nm) are also referred to as nanoparticles. Any of a variety of materials can be used to form or provide particles, as will be understood by those of skill in the art. In some embodiments, particular materials and/or shapes may be preferred based on chemistries or other features utilized in relevant embodiments; those of ordinary skill will be well familiar with various options and parameters guiding selection. In many embodiments, suitable materials include, but are not limited to, plastics, ceramics, glass, polystyrene, methylstyrene, acrylic polymers, metal, paramagnetic materials, thoria sol, graphitic carbon, titanium dioxide, latex or cross-linked dextrans such as Sepharose, cellulose, nylon, cross-linked micelles and teflon. In some embodiments, particles can be optically or magnetically detectable. In some embodiments, particles contain fluorescent or luminescent moieties, or other detectable moieties.

The term "signal" used herein refers to a detectable and/or measurable event. In certain embodiments, a signal is detectable by the human eye, e.g., visible. In certain embodiments, detection of a signal requires an apparatus other than human eyes. In some embodiments, a signal may be or comprise electromagnetic radiation or a feature (e.g., wavelength, intensity). In some embodiments, a signal is an optical signal. A signal may be or comprises light (e.g., visible light and/or ultraviolet light). For example, a signal can be light generated by a chemiluminescent reaction. Typically, light can be detectable by a spectrophotometer. In some embodiments, a signal is or relates to radiation, e.g., radiation emitted by radioisotopes, infrared radiation, etc. In certain embodiments, a signal is a direct or indirect indicator of a property of a physical entity. For example, a signal could be used as an indicator of amount and/or concentration of a nucleic acid in a biological sample and/or in a reaction vessel.

The term "substantially" as used herein refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" may be used herein to capture the potential lack of completeness inherent in many biological and chemical phenomena.

DETAILED DESCRIPTION OF CERTAIN EMBODIMENTS

The term "digital" is general used to refer to the nature of discrete (discontinuous) values. As a person of ordinary skill in the art of life sciences will appreciate, a digital analysis used herein can refer to a quantification based on processing of digital signals of an analyte and/or its change. Any appropriate means and/or system can be utilized in accordance with the present invention to detect and/or quantify an analyte and/or its change (e.g., an event of interest) directly or indirectly. To give an example, a blinking agent such as quantum dots can be used to general signals.

Signals, in a broad sense, comprise signals of analytes/event and noises (e.g. background signals). In some embodiments, a signal refers to that of an analyte/event, that is, signal of interest. In some embodiments, provided methods and systems herein are used to improve signal-to-noise ratios (i.e., ratios of signal of interest to background signal). In certain embodiments, variation of signal of interest is processed over time compared to variations in background signals, such that the signal of interest is distinguishable from those of the background signals.

In some embodiments, provided methodologies enable quantification of analytes present in a sample at a single-molecule level or at a level of subfemtomolar concentration. The present disclosure, among other things, encompasses the recognition that one challenge with many commonly employed single molecule analysis methodologies is that the extreme dilutions utilized to ensure that only a single molecule is present can make it difficult to isolate enough molecules for detection, as the probability of finding a single molecule in a dilute solution is low. The present invention not only identifies the source of this problem, but provides a solution by providing technologies that localize individual molecules that are present in dilute solution onto a substrate, which can then be optionally amplified/concentrated, and identify/count.

In accordance with the present disclosure, a digital analysis, in some embodiments, is particularly useful in detection and/or quantification of single molecules. In some embodiments, provided methods and systems herein, in addition to a digital analysis, further comprise other processes (e.g., chemical, physical and/or digital, etc.).

Referring to FIG. 1, a flow chart of an example method for analysis, in some embodiments, may begin with sample preparation. Analytes can be distributed onto an imaging substrate to achieve single molecules at discrete locations. In some embodiments, analytes are blinking agents. In some embodiments, analytes are not blinking agents and are contacted with blinking agents. Blinking agents are optically detectable in some embodiments, and sets of imaging data are collected over time (e.g., at least a first and a second time points).

Imaging data sets can be provided to a process of a computing device. The process, in some embodiments, analyze data sets to obtain resulting data reflecting signal variation. In certain embodiments, resulting data are or comprise standard deviation, sum and any combination thereof. In certain embodiments, resulting data are further processed.

Using an algorithm, a threshold for signal variation can be determined. In some embodiments, when the resulting data at a particular location are greater than threshold, the location is determined to be a positive count. A positive count can reflect the presence of a single molecule analyte. In other embodiments, when the resulting data are less than threshold, it represents background signal, which reflects that the location does not contain a single molecule analyte. the location is determined to be a positive count. A positive count can reflect the presence of a single molecule analyte.

Prior to providing data or after establishing locations, provided method herein may further include validating or processing the data using any other methods. In some embodiments, method may further include determining, by more processors, based upon the resulting data and more algorithms. In some embodiments, method may further include retrieving, from a second storage medium, data, for example, data of calibration curves.

Blinking Agent

As defined above, a blinking agent utilized in accordance with the present disclosure is an entity characterized by a stochastic detectable feature. In various embodiments, a blinking agent is characterized by a feature whose detectable attribute varies stochastically relative to time. In some embodiments, a blinking agent is directly detectable; in some embodiments, it is indirectly detectable.

In some embodiments, particles are blinking agents. Particles can be detectable directly due to their intrinsic properties or indirect (e.g., via additional processes/agents).

Particles

Where particles are used in the practice of the present invention, it is not intended that the present invention be limited to a particular material. A variety of particle materials are commercially available, including but not limited to, particles selected from agarose beads, streptavidin-coated beads, NeutrAvidin-coated beads, antibody-coated beads, paramagnetic beads, magnetic beads, electrostatic beads, electrically conducting beads, fluorescently labeled beads, colloidal beads, glass beads, semiconductor beads, and polymeric beads.

Particles useful in accordance with the present invention need not be spherical; irregular particles and/or particles having non-spherical shapes, may be used.

A population of particles can be but need not be relatively uniform in terms of size, shape, and/or composition. Particles can have a variety of different shapes including spheres, oblate spheroids, cylinders, ovals, ellipses, shells, cubes, cuboids, cones, pyramids, rods (e.g., cylinders or elongated structures having a square or rectangular cross-section), tetrapods (particles having four leg-like appendages), triangles, prisms, etc.

Particles can be solid or hollow and can comprise one or more layers (e.g., nanoshells, nanorings, etc.). Particles may have a core/shell structure, wherein the core(s) and shell(s) can be made of different materials. Particles may comprise gradient or homogeneous alloys. Particles may be composite particles made of two or more materials, of which one, more than one, or all of the materials possess magnetic properties, electrically detectable properties, and/or optically detectable properties.

In certain embodiments of the invention, a particle is porous, by which is meant that the particle contains holes or channels, which are typically small compared with the size of a particle. For example a particle may be a porous silica particle, e.g., a mesoporous silica particle or may have a coating of mesoporous silica.

In some embodiments, particles are biocompatible. Additionally or alternatively, particles may have a coating layer. Use of a biocompatible coating layer can be advantageous in some embodiments. Suitable coating materials include, but are not limited to, natural proteins such as bovine serum albumin (BSA), biocompatible hydrophilic polymers such as polyethylene glycol (PEG) or a PEG derivative, phospholipid-(PEG), silica, lipids, polymers, carbohydrates such as dextran, other materials that can be associated with particles, etc. Coatings may be applied or assembled in a variety of ways such as by dipping, using a layer-by-layer technique, by self-assembly, conjugation, etc.

In some embodiments, polymeric particles may be used in accordance with the present invention. For example, particles can be made of organic polymer including, but not limiting to, polystyrene, polymethylmethacrylate, polyacrylamide, poly(vinyl chloride), carboxylated poly(vinyl chloride), poly(vinyl chloride-co-vinyl acetate-co-vinyl alcohol), and combination thereof. Additionally or alternatively, particles can be or comprises inorganic polymers such as silica ($SiO_2$).

Quantum Dots

In some embodiments, particles are or comprise intrinsically fluorescent or luminescent particles. In certain embodiments, particles are or comprise quantum dots (QDs).

QDs are bright, fluorescent nanocrystals with physical dimensions small enough such that the effect of quantum confinement gives rise to unique optical and electronic properties. Semiconductor QDs are often composed of atoms from groups II-VI or III-V in the periodic table, but other compositions are possible. By varying their size and composition, the emission wavelength can be tuned (i.e., adjusted in a predictable and controllable manner) from the blue to the near infrared. QDs generally have a broad absorption spectrum and a narrow emission spectrum. Thus different QDs having distinguishable optical properties (e.g., peak emission wavelength) can be excited using a single source. In general, QDs are brighter and photostable than most conventional fluorescent dyes. QDs and methods for their synthesis are well known in the art (see, e.g., U.S. Pat. Nos. 6,322,901; 6,576,291; and 6,815,064; all of which are incorporated herein by reference). QDs can be rendered water soluble by applying coating layers comprising a variety of different materials (see, e.g., U.S. Pat. Nos. 6,423,551; 6,251,303; 6,319,426; 6,426,513; 6,444,143; and 6,649,138; all of which are incorporated herein by reference). For example, QDs can be solubilized using amphiphilic polymers. Exemplary polymers that have been employed include octylamine-modified low molecular weight polyacrylic acid, polyethylene-glycol (PEG)-derivatized phospholipids, polyanhydrides, block copolymers, etc.

Exemplary QDs suitable for use in accordance with the present invention in some embodiments, include ones with a wide variety of absorption and emission spectra and they are commercially available, e.g., from Quantum Dot Corp. (Hayward Calif.; now owned by Invitrogen) or from Evident Technologies (Troy, N.Y.). For example, QDs having peak emission wavelengths of approximately 525 nm, approximately 535 nm, approximately 545 nm, approximately 565 nm, approximately 585 nm, approximately 605 nm, approximately 655 nm, approximately 705 nm, and approximately 800 nm are available. Thus QDs can have a range of different colors across the visible portion of the spectrum and in some cases even beyond.

Additionally or alternatively, particles can be functionalized (e.g., surface functionalized by adsorption or covalently bonding) or "doped" or "loaded" with fluorescent and luminescent moieties (e.g., fluorescent dyes) for optical characterization. Examples of fluorescent dyes include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. In addition to or alternative to single optical moieties, encoding can be accomplished in a ratio of at least two moieties.

In certain embodiments, optically detectable particles are or comprise metal particles. Metals of use include, but are not limited to, gold, silver, iron, cobalt, zinc, cadmium, nickel, gadolinium, chromium, copper, manganese, palladium, tin, and alloys thereof. Oxides of any of these metals can be used.

Certain metal particles, referred to as plasmon resonant particles, exhibit the well known phenomenon of plasmon resonance. The features of the spectrum of a plasmon resonant particle (e.g., peak wavelength) depend on a number of factors, including the particle's material composition, the shape and size of the particle, the refractive index or dielectric properties of the surrounding medium, and the presence of other particles in the vicinity. Selection of particular particle shapes, sizes, and compositions makes it possible to produce particles with a wide range of distinguishable optically detectable properties thus allowing for concurrent detection of multiple nucleic acids by using particles with different properties such as peak scattering wavelength.

Magnetic properties of particles can be used in accordance with the present invention. Particles in some embodiments are or comprise magnetic particles, that is, magnetically responsive particles that contain one or more metals or oxides or hydroxides thereof. Magnetic particles may comprise one or more ferrimagnetic, ferromagnetic, paramagnetic, and/or superparamagnetic materials. Useful particles may be made entirely or in part of one or more materials selected from the group consisting of: iron, cobalt, nickel, niobium, magnetic iron oxides, hydroxides such as maghemite ($\gamma$-$Fe_2O_3$), magnetite ($Fe_3O_4$), feroxyhyte (FeO(OH)), double oxides or hydroxides of two- or three-valent iron with two- or three-valent other metal ions such as those from the first row of transition metals such as Co(II), Mn(II), Cu(II), Ni(II), Cr(III), Gd(III), Dy(III), Sm(III), mixtures of the afore-mentioned oxides or hydroxides, and mixtures of any of the foregoing. See, e.g., U.S. Pat. No. 5,916,539 (incorporated herein by reference) for suitable synthesis methods for certain of these particles. Additional materials that may be used in magnetic particles include yttrium, europium, and vanadium.

Signal Collection

Any appropriate means and/or system for collecting signals can be utilized in accordance with the present invention. Detection and/or quantification can comprise a step of counting the number of single molecule analytes that is determined as a positive count. Such counting can determine the quantity of analytes in samples.

To give but a few examples, detectable signals may include, but are not limited to, signals from radioisotopes, fluorophores, chromophores, electron dense particles, magnetic particles, spin labels, molecules that emit chemiluminescence, electrochemically active molecules, enzymes, cofactors, enzymes linked to nucleic acid probes and enzyme substrates.

In some embodiments, a signal is a detectable property that is generated or changed, of and/or around a blinking agent. Those of ordinary skill in the art will appreciate that, in some embodiments, actual detection or development of a generated or changed detectable property may require or involve one or more additional steps (e.g., binding of a labeled moiety to an amplified nucleic acid, or to a particle containing an amplified nucleic acid, interaction with a reactant (e.g., electromagnetic radiation, an enzyme, a reagent, or a combination of these) that triggers a detectable event from an analyte or a blinking agent which one of these has interacted, etc). Such steps are well known in the art.

In some embodiments, a detectable property is optical. Exemplary optical properties include, but are not limited to, fluorescent, ultraviolet, infrared, holographic, radiographic signals and any combination thereof. An optical property, in some embodiments, can be detected through absorption, emission, reflection, refraction, interference, diffraction, dispersion, scattering, or any combination thereof, etc. In many embodiments, a signal is presence or change of florescence.

In some embodiments, optical imaging is used in accordance with the present invention. Illustrative optical detection methodologies include, but are not limited to, light scattering, multichannel fluorescence detection, UV and visible wavelength absorption, luminescence, differential reflectivity, and confocal laser scanning Additional detection methods that can be used in certain applications include scintillation proximity assay (SPA) techniques, radiochemical detection, fluorescence polarization, fluorescence correlation spectroscopy (FCS), time-resolved energy transfer (TRET), fluorescence resonance energy transfer (FRET) and variations such as bioluminescence resonance energy transfer (BRET). Additional or alternative detection options include electrical resistance, resistivity, impedance, and voltage sensing.

Applications

The present invention has many applications, including, but not limited to, diagnosis and monitoring in medicine and any non-medical applications, where the presence and/or the amount of an analyte can be determined. In some embodiments, the presence or the amount of an analyte is determined using the present invention. In certain embodiments, an analyte is a nucleic acid (e.g., DNA and RNA).

Those of ordinary skill reading the present disclosure, will appreciate its broad applicability. In some embodiments, provided methods herein are used to detect and/or quantify analytes, for example, to profile a specific tissue or a specific condition. In some embodiments, provided methods herein are used to detect and/or quantify analytes to detect biomarkers for specific tissue or condition. In certain embodiments, provided methods herein are used to detect and/or quantify analytes to profile a neoplastic and/or cancer cell.

For example, a wide variety of infectious diseases can be detected and/or determined by the process of the present invention, for example, those caused by bacterial, viral, parasite, and fungal infectious agents. The resistance of various infectious agents to drugs can also be determined using the present invention.

Representative bacterial infectious agents which can be detected and/or determined by the present invention include, but are not limited to, *Escherichia coli, Salmonella, Shigella, Klebsiella, Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia*, B-Hemolytic strep., *Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis*, Rickettsial pathogens, *Nocardia*, and *Acitnomycetes*.

Representative fungal infectious agents which can be detected and/or determined by the present invention include, but are not limited to, *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis*, and *Maduromycosis*.

Representative viral infectious agents which can be detected and/or determined by the present invention include, but are not limited to, human immunodeficiency virus, human T-cell lymphocytotrophic virus, hepatitis viruses (e.g., Hepatitis B Virus and Hepatitis C Virus), Epstein-Barr Virus, cytomegalovirus, influenza viruses, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Representative parasitic agents which can be detected and/or determined by the present invention include, but are not limited to, *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichimonas* spp., *Balatidium coli, Wuchereria ban-*

*crofti*, *Toxoplasma* spp., *Enterobius vermicularis*, *Ascaris lumbricoides*, *Trichuris trichiura*, *Dracunculus medinesis*, trematodes, *Diphyllobothrium latum*, *Taenia* spp., *Pneumocystis carinii*, and *Necator americanis*.

The present invention can also be useful for detection and/or determination of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can be identified with the present invention.

Genetic diseases can also be detected and/or determined by the process of the present invention. This can be carried out by prenatal or post-natal screening for chromosomal and genetic aberrations or for genetic diseases. Examples of detectable genetic diseases include, but are not limited to: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

Cancers which can be detected and/or determined by the process of the present invention generally involve oncogenes, tumor suppressor genes, or genes involved in DNA amplification, replication, recombination, or repair. Examples of these include, but are not limited to: BRCA1 gene, p53 gene, APC gene, Her2/Neu amplification, Bcr/Ab1, K-ras gene, and human papillomavirus Types 16 and 18. Various aspects of the present invention can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In the area of environmental monitoring, the present invention can be used, for example, for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can also be used in a variety of forensic areas, including, for example, for human identification for military personnel and criminal investigation, paternity testing and family relation analysis, HLA compatibility typing, and screening blood, sperm, or transplantation organs for contamination.

In the food and feed industry, the present invention has a wide variety of applications. For example, it can be used for identification and characterization of production organisms such as yeast for production of beer, wine, cheese, yoghurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections.

Kits

A variety of assays known in the art can be used in accordance with the present disclosure. Also provided are kits for carrying out the methods and/or assays described herein.

In some embodiments, the kit further comprises instructions for analysis, interpretation and/or dissemination of data acquired by the kit. In some embodiments, instructions for the operation, analysis, interpretation and dissemination of the data of the kit are provided on computer readable media.

In some embodiments, a kit comprises one or more reagents for optical characterization. For example, a fluorescent or other optically labeled probes that comprise at least a complementary sequence to a target nucleic acid used in accordance with the methods herewith.

A kit may include instructions pertinent for the particular embodiment of the kit, such instructions describing incubation and/or amplification conditions for operation of assays. A kit may also comprise reaction containers such as microcentrifuge tubes, microtiter plates, and the like. A kit may also comprise reagents or other materials for preparing samples and/or performing methods, including, for example, detergents, solvents, or ion exchange resins.

Network and Computer Device

Figure 2:
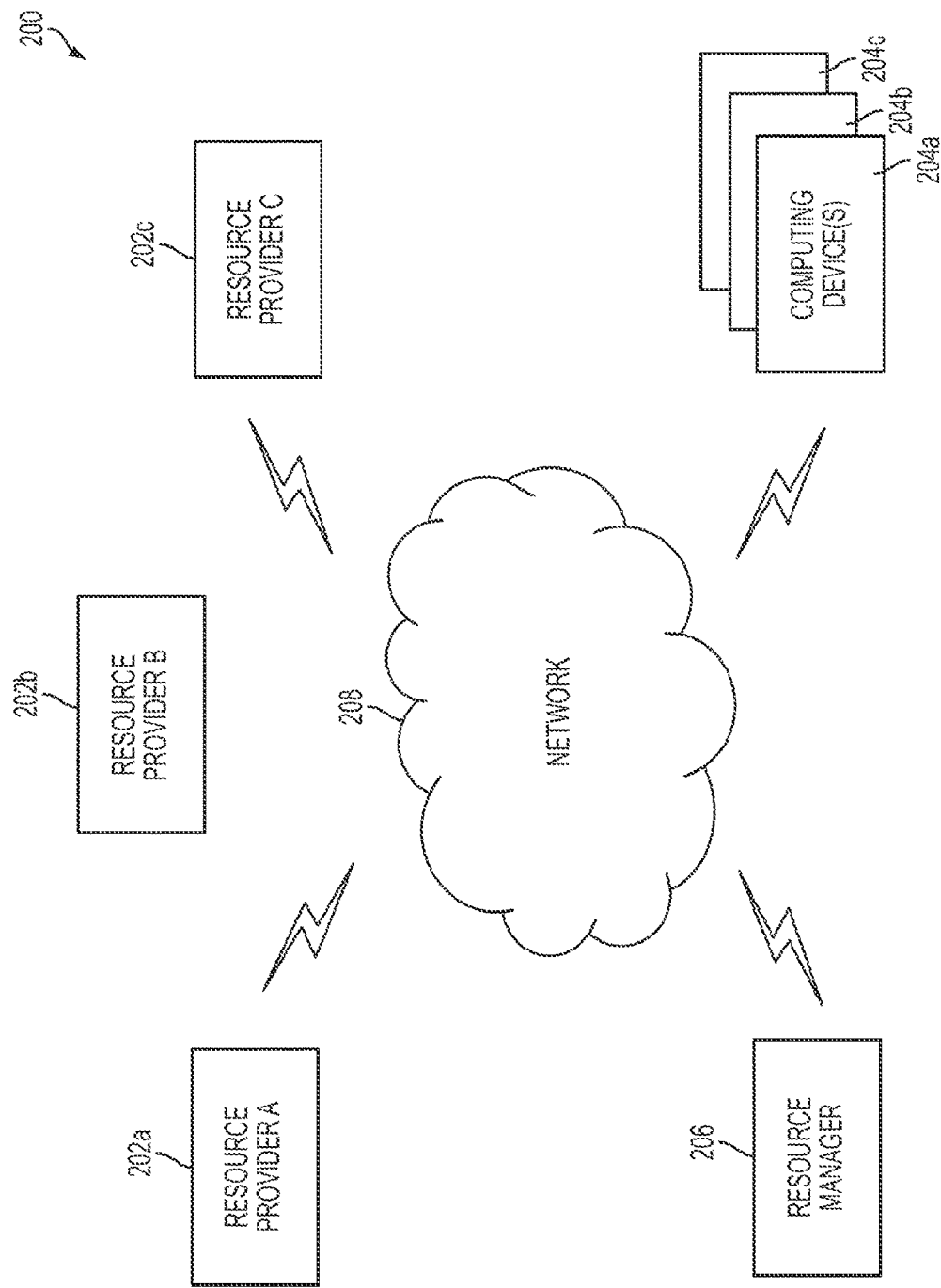
FIG. 2 is a block diagram of an example network environment.

As shown in FIG. 2, an implementation of an exemplary cloud computing environment 200 for analysis data is shown and described. The cloud computing environment 200 may include one or more resource providers 202a, 202b, 202c (collectively, 202). Each resource provider 202 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 202 may be connected to any other resource provider 202 in the cloud computing environment 200. In some implementations, the resource providers 202 may be connected over a computer network 208. Each resource provider 202 may be connected to one or more computing device 204a, 204b, 204c (collectively, 204), over the computer network 208.

The cloud computing environment 200 may include a resource manager 206. The resource manager 206 may be connected to the resource providers 202 and the computing devices 204 over the computer network 208. In some implementations, the resource manager 206 may facilitate the provision of computing resources by one or more resource providers 202 to one or more computing devices 204. The resource manager 206 may receive a request for a computing resource from a particular computing device 204. The resource manager 206 may identify one or more resource providers 202 capable of providing the computing resource requested by the computing device 204. The resource manager 206 may select a resource provider 202 to provide the computing resource. The resource manager 206 may facilitate a connection between the resource provider 202 and a particular computing device 204. In some implementations, the resource manager 206 may establish a connection between a particular resource provider 202 and a particular computing device 204. In some implementations, the resource manager 206 may redirect a particular computing device 204 to a particular resource provider 202 with the requested computing resource.

Figure 3:
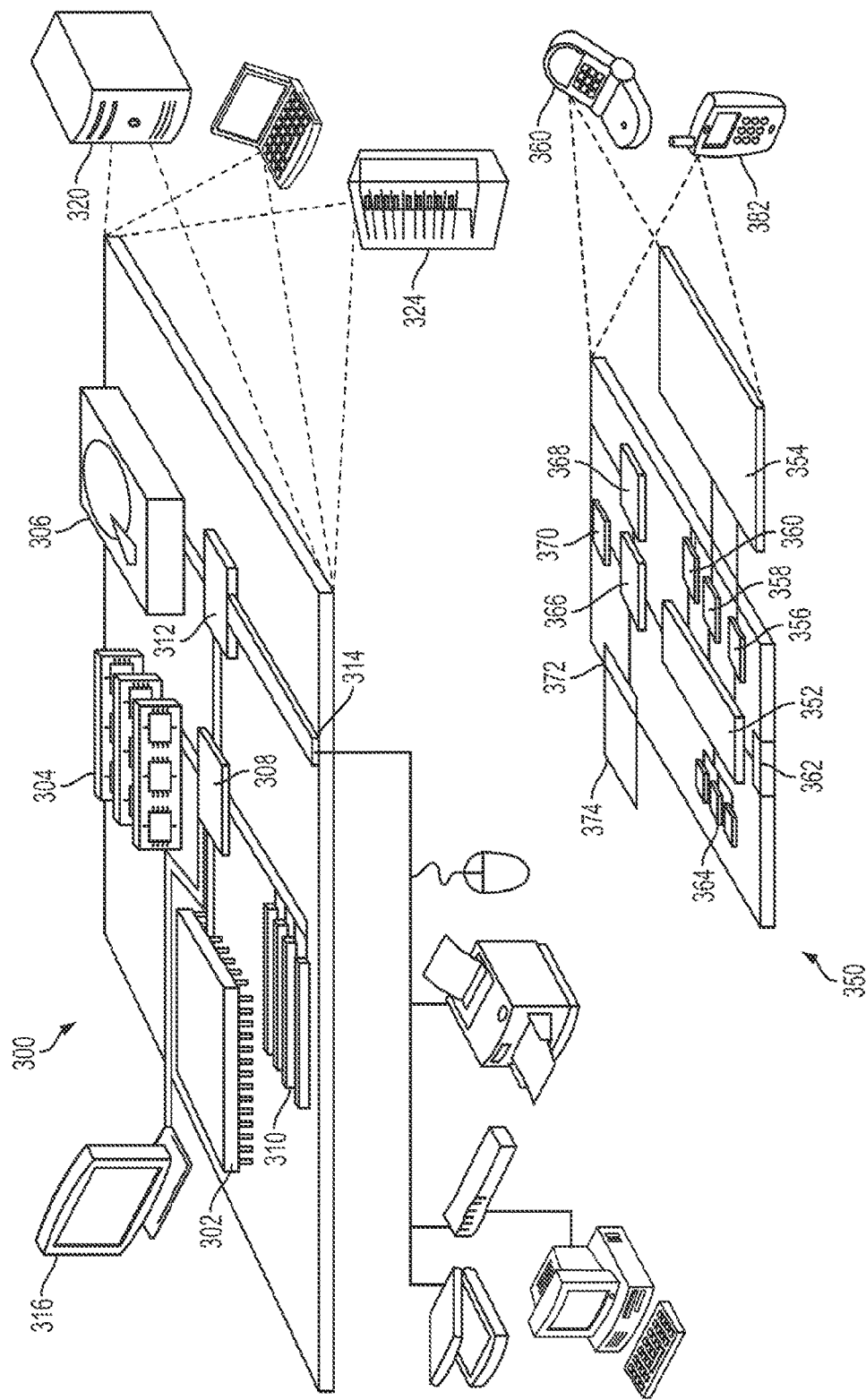
FIG. 3 is a block diagram of a computing device and a mobile computing device.

FIG. 3 shows an example of a computing device 300 and a mobile computing device 250 that can be used to implement the techniques described in this disclosure. The computing device 200 is intended to represent various forms of digital computers, such as laptops, desktops, workstations, personal digital assistants, servers, blade servers, mainframes, and other appropriate computers. The mobile computing device 250 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 200 includes a processor 202, a memory 204, a storage device 206, a high-speed interface 208 connecting to the memory 204 and multiple high-speed expansion ports 210, and a low-speed interface 212 connecting to a low-speed expansion port 214 and the storage device 206. Each of the processor 202, the memory 204, the storage device 206, the high-speed interface 208, the high-speed expansion ports 210, and the low-speed interface 212, are interconnected using various busses, and may be mounted on a common motherboard or in other manners as appropriate. The processor 202 can process instructions for execution within the computing device 200, including instructions stored in the memory 204 or on the storage device 206 to display graphical information for a GUI on an external input/output device, such as a display 216 coupled to the high-speed interface 208. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 204 stores information within the computing device 200. In some implementations, the memory 204 is a volatile memory unit or units. In some implementations, the memory 204 is a non-volatile memory unit or units. The memory 204 may also be another form of computer-readable medium, such as a magnetic or optical disk.

The storage device 206 is capable of providing mass storage for the computing device 200. In some implementations, the storage device 206 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 202), perform one or more methods, such as those described above. The instructions can also be stored by one or more storage devices such as computer- or machine-readable mediums (for example, the memory 204, the storage device 206, or memory on the processor 202).

The high-speed interface 208 manages bandwidth-intensive operations for the computing device 200, while the low-speed interface 212 manages lower bandwidth-intensive operations. Such allocation of functions is an example only. In some implementations, the high-speed interface 208 is coupled to the memory 204, the display 216 (e.g., through a graphics processor or accelerator), and to the high-speed expansion ports 210, which may accept various expansion cards (not shown). In the implementation, the low-speed interface 212 is coupled to the storage device 206 and the low-speed expansion port 214. The low-speed expansion port 214, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 200 may be implemented in a number of different forms, as shown in the figure. For example, it may be implemented as a standard server 220, or multiple times in a group of such servers. In addition, it may be implemented in a personal computer such as a laptop computer 222. It may also be implemented as part of a rack server system 224. Alternatively, components from the computing device 200 may be combined with other components in a mobile device (not shown), such as a mobile computing device 250. Each of such devices may contain one or more of the computing device 200 and the mobile computing device 250, and an entire system may be made up of multiple computing devices communicating with each other.

The mobile computing device 250 includes a processor 252, a memory 264, an input/output device such as a display 254, a communication interface 266, and a transceiver 268, among other components. The mobile computing device 250 may also be provided with a storage device, such as a micro-drive or other device, to provide additional storage. Each of the processor 252, the memory 264, the display 254, the communication interface 266, and the transceiver 268, are interconnected using various buses, and several of the components may be mounted on a common motherboard or in other manners as appropriate.

The processor 252 can execute instructions within the mobile computing device 250, including instructions stored in the memory 264. The processor 252 may be implemented as a chipset of chips that include separate and multiple analog and digital processors. The processor 252 may provide, for example, for coordination of the other components of the mobile computing device 250, such as control of user interfaces, applications run by the mobile computing device 250, and wireless communication by the mobile computing device 250.

The processor 252 may communicate with a user through a control interface 258 and a display interface 256 coupled to the display 254. The display 254 may be, for example, a TFT (Thin-Film-Transistor Liquid Crystal Display) display or an OLED (Organic Light Emitting Diode) display, or other appropriate display technology. The display interface 256 may include appropriate circuitry for driving the display 254 to present graphical and other information to a user. The control interface 258 may receive commands from a user and convert them for submission to the processor 252. In addition, an external interface 262 may provide communication with the processor 252, so as to enable near area communication of the mobile computing device 250 with other devices. The external interface 262 may provide, for example, for wired communication in some implementations, or for wireless communication in other implementations, and multiple interfaces may also be used.

The memory 264 stores information within the mobile computing device 250. The memory 264 can be implemented as one or more of a computer-readable medium or media, a volatile memory unit or units, or a non-volatile memory unit or units. An expansion memory 274 may also be provided and connected to the mobile computing device 250 through an expansion interface 272, which may include, for example, a SIMM (Single In Line Memory Module) card interface. The expansion memory 274 may provide extra storage space for the mobile computing device 250, or may also store applications or other information for the mobile computing device 250. Specifically, the expansion memory 274 may include instructions to carry out or supplement the processes described above, and may include secure information also. Thus, for example, the expansion memory 274 may be provide as a security module for the mobile computing device 250, and may be programmed with instructions that permit secure use of the mobile computing device 250. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 252), perform one or more methods, such as those described above. The instructions can also be stored by one or more storage devices, such as one or more computer- or machine-readable mediums (for example, the memory 264, the expansion memory 274, or memory on the processor 252). In some implementations, the instructions can be received in a propagated signal, for example, over the transceiver 268 or the external interface 262.

The mobile computing device 250 may communicate wirelessly through the communication interface 266, which may include digital signal processing circuitry where necessary. The communication interface 266 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 268 using a radio-frequency. In addition, short-range communication may occur, such as using a Bluetooth®, Wi-Fi™, or other such transceiver (not shown). In addition, a GPS (Global Positioning System) receiver module 270 may provide additional navigation- and location-related wireless data to the mobile computing device 250, which may be used as appropriate by applications running on the mobile computing device 250.

The mobile computing device 250 may also communicate audibly using an audio codec 260, which may receive spoken information from a user and convert it to usable digital information. The audio codec 260 may likewise generate audible sound for a user, such as through a speaker, e.g., in a handset of the mobile computing device 250. Such sound may include sound from voice telephone calls, may include recorded sound (e.g., voice messages, music files, etc.) and may also include sound generated by applications operating on the mobile computing device 250.

The mobile computing device 250 may be implemented in a number of different forms, as shown in the figure. For example, it may be implemented as a cellular telephone 280. It may also be implemented as part of a smart-phone 282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In view of the structure, functions and apparatus of the systems and methods described here, in some implementations, a system and method for analysis of data are provided. Having described certain implementations of methods and apparatus for supporting analysis of data, it will now become apparent to one of skill in the art that other implementations incorporating the concepts of the disclosure may be used. Therefore, the disclosure should not be limited to certain implementations, but rather should be limited only by the spirit and scope of the following claims.

EXEMPLIFICATION

Example 1

Assessing the Stochastic Intermittency of Single Quantum Dot Luminescence

This Example presents a methodology for digital quantification (e.g., of biomolecules) by detecting the variations in the signal from a blinking agent, for example, single quantum dot reporters. The method takes advantage of the stochastic blinking process intrinsic of the Quantum dots (QDs) to measure the variation and compare it to the variations of the background.

Methods and Materials

PEG-SVA Functionalization on Amino-silanized Glass in PDMS Wells

The early platform consisted of making wells out of a poly-dimethylsiloxane (PDMS) block fixed on a glass coverslip. Glass coverslips (No. 1.5 24×40 mm, Fisher Scientific #12-544-C, glass thickness 0.16-0.19 mm) can be cleaned and functionalized separately and PDMS blocks with wells cut out are fixed individually. All reagents were purchased from Sigma-Aldrich at molecular biology grade unless otherwise specified. QDot 585 Streptavidin Conjugate was purchased from Invitrogen Corp (catalog number Q10111MP). PEG reagents were purchased from Laysan Bio, Inc.

Coverslips were cleaned by successive sonication in a glass staining dish for 20 minutes in 10% Alconox suspension, 5 minutes in Milli-Q water, 10 minutes in acetone, 15 minutes in 1M KOH, 10 minutes in Milli-Q water. Cleaned slides were stored in Milli-Q water until use. Silanization with 3-aminopropyl triethoxysilane (APTES) was carried out in a plastic staining dish with a mixture of 50 mL methanol, 2.5 mL acetic acid, and 0.5 mL APTES for 20 minutes, with sonication for one minute after the first ten minutes of reaction.

Figure 4:
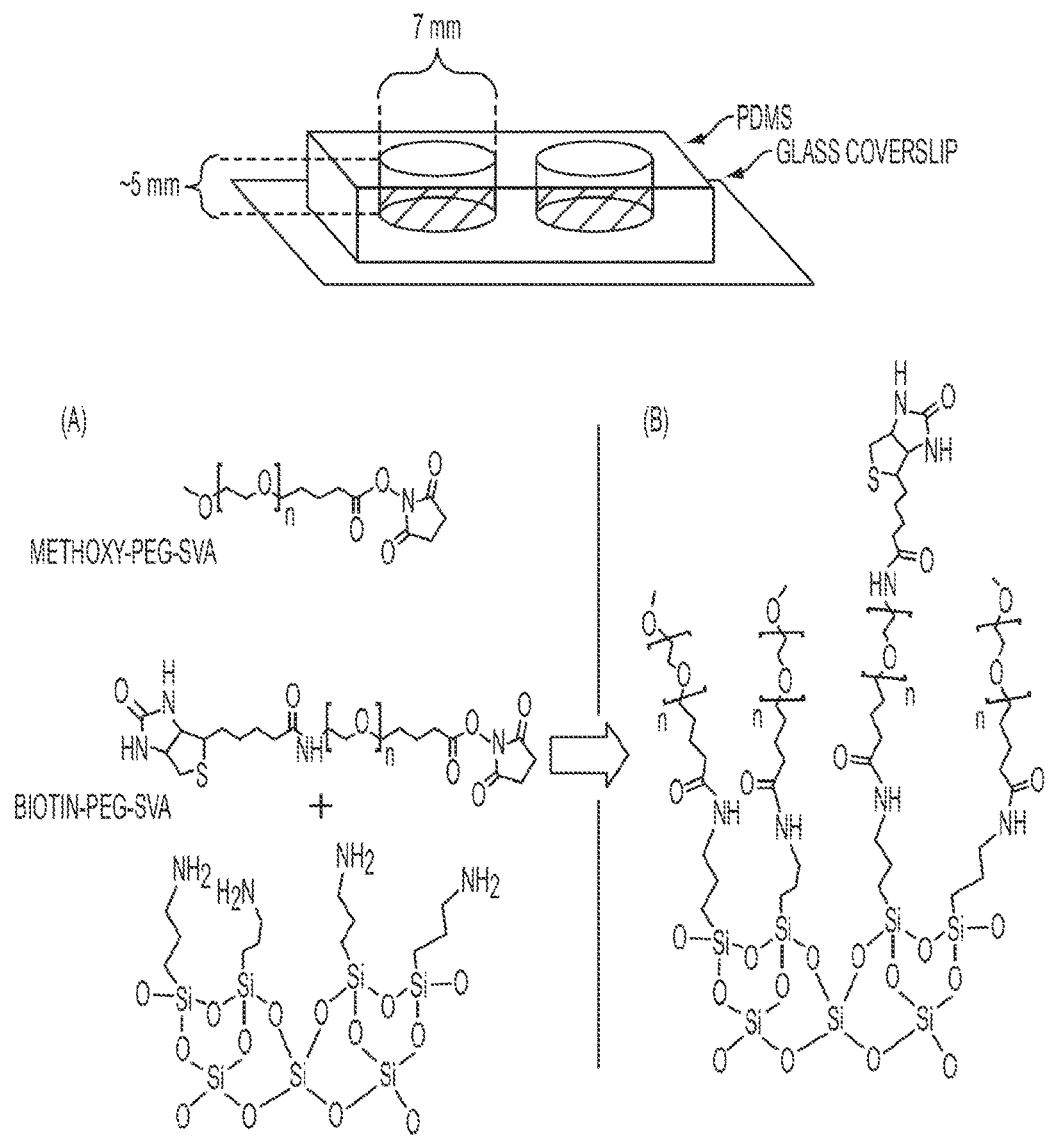
FIG. 4: Top: PDMS wells on glass coverslip for PEG-biotin functionalization for SA-QD immobilization. Glass coverslips are cleaned and silanized before affixing PDMS wells. PEGylation and subsequent SA-QD binding is carried out in wells. Bottom: Surface chemistry scheme. PEG-SVA reagents react with amine groups on glass (A), producing amide linkages (B) with biotin groups scattered on surface. For PEG MW 5000 g/mol, average length n=114.

PDMS was prepared by 10:1 mixture of PDMS base and elastomer, centrifuged at 1860×g for 2 minutes to remove bubbles, poured onto a flat petri dish, degassed under vacuum and cured 1 hour at 80° C. Holes for the wells were cut using a hole-punch, creating two 7 mm-diameter holes in a piece of PDMS polymer. The PDMS pieces were exposed to air plasma treatment for 1 minute and immediately pressed onto cleaned, silanized, and dried coverslips to bond. A schematic of this assembly is shown in FIG. 4. Wells produced in this way have a base surface area of 38.5 mm$^2$ and hold approximately 100 μL, though the well volume can vary as the thickness is determined when the PDMS layer is cast.

For these experiments, the poly-(ethylene glycol) (PEG) surface was deposited by PEG modified with succinimidyl valerate ester (PEG-SVA). The reaction chemistry scheme is depicted in FIG. 4 below. The reaction mixture was prepared in a 40:1 ratio of methoxy-PEG-SVA and biotin-PEG-SVA, using 12.5 mg mPEG-SVA (MW 5000) and 0.31 mg biotin-PEG-SVA (MW 5000) per 100 μL of 0.1 M NaHCO$_3$ solution (pH 8.25) (concentrations 250 μM mPEG-SVA and 6.2 μM biotin-PEG-SVA). The solution was mixed thoroughly and centrifuged at 7200 g for 1 minute to remove bubbles. 40 μL of this mixture was added to each well and allowed to react overnight in a dark, humid chamber.

After this reaction, wells were washed with Milli-Q water. Surfaces were blocked by treating with 40 μL of BSA blocking solution (1% BSA in PBS) for 1 hour. This solution was removed and 40 μL of streptavidin-conjugated QD (SA-QD) solution (prepared at various dilutions in PBS with 1% BSA) was added to each well and allowed 15 minutes for surface binding. The SA-QD solution was removed and wells were washed three times with borate buffer (Thermo Scientific, contains 50 mM borate, pH 8.5)) and then filled with borate buffer for imaging.

Samples were imaged using a Hamamatsu ImagEM EM-CCD camera on an Olympus IX-71 microscope configured for TIRF microscopy. The field of view with this configuration is 135 μm by 135 μm. Illumination source was a Melles Griot 561 nm diode-pumped solid-state laser, introduced through an Olympus APON 60xO TIRF objective (1.49 NA). Images were recorded as 500 frame movies, at 32 frames/sec (approximately 15 sec total observation time) with sensitivity gain 180.

Image Processing and Analysis

All image processing and analysis was carried out using the open source Java-based software ImageJ (v. 1.44p, National Institutes of Health, http://imagej.nih.gov/ij). This section describes the steps in the image processing and analysis to determine the number of QDs in a sample field of view taken on the microscope. The image processing and analysis described here were automated in a self-written macro using ImageJ built-in functions. This automation provides a consistent analysis unbiased by a human counter while greatly reducing the time for analysis.

Figure 5:
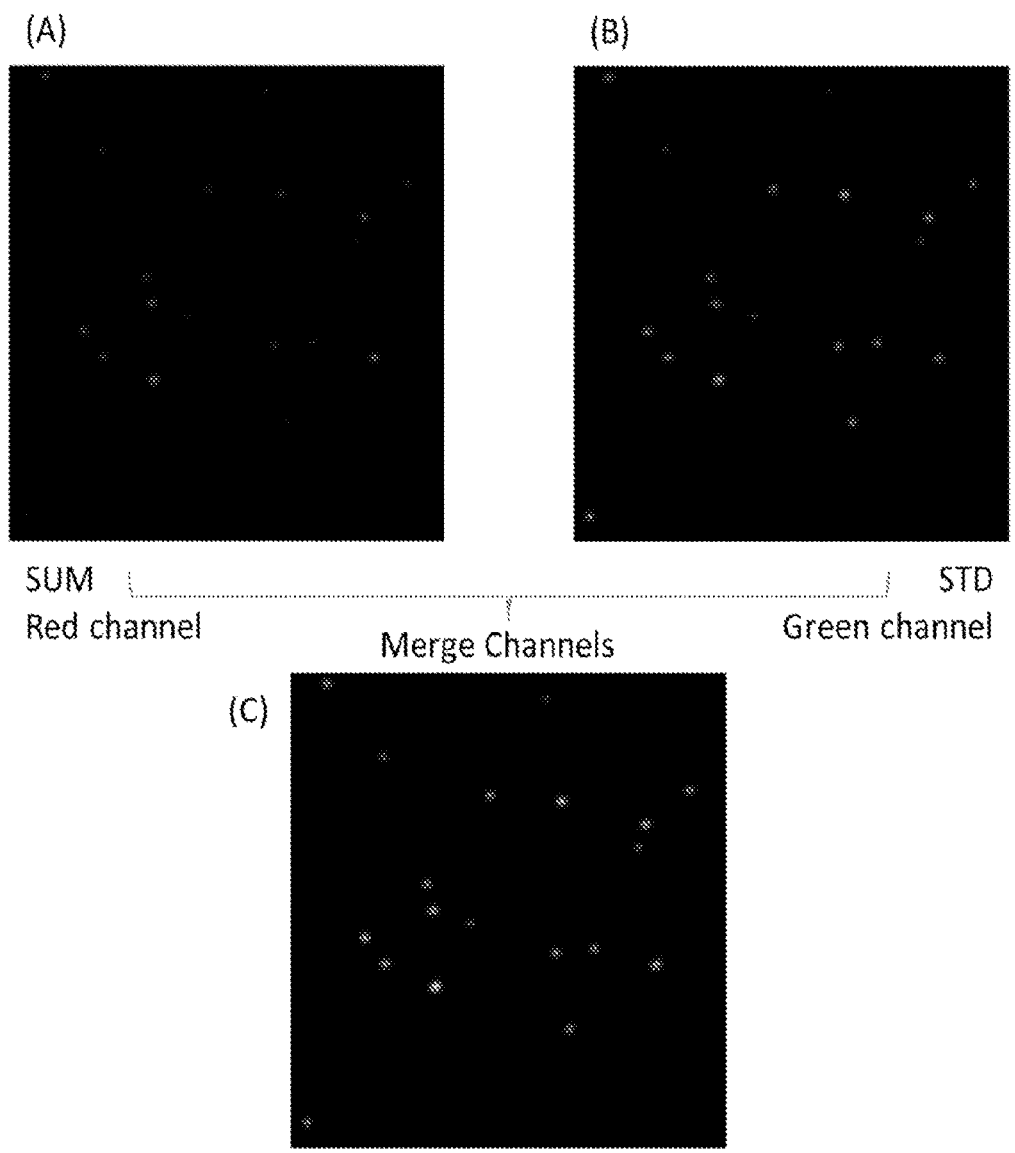
FIG. 5: Merging SUM and STD projections. (A) and (B) are SUM and STD projections of the same sample image. Particles in the merged image (C) which appear more green were more intense in the STD projection, and vice versa. For example the particle at the bottom left, which is hardly visible in the SUM projection, is detected due to its high signal in the STD projection.

Image sequences were taken by collecting 500 frames at 30.5 msec exposure time (~32 frames/sec) and converted into 16-bit depth multi-page TIFF movie files. To take advantage of the intermittent signal from QD reporters, we use the Standard Deviation projection instead of simply the Sum projection. This operation creates a projection image by calculating the standard deviation of each pixel's set of values through the stack. In order to improve detection of QDs with varying brightness and blinking behaviors, the Sum and Standard Deviation methods are both applied and the two resulting projections are normalized and merged into one composite image using the Merge Channels function. This process is illustrated in FIG. 5 (the image used in the figures here is a subset of a data image, showing only a region 1/16 of the full field of view).

Figure 6:
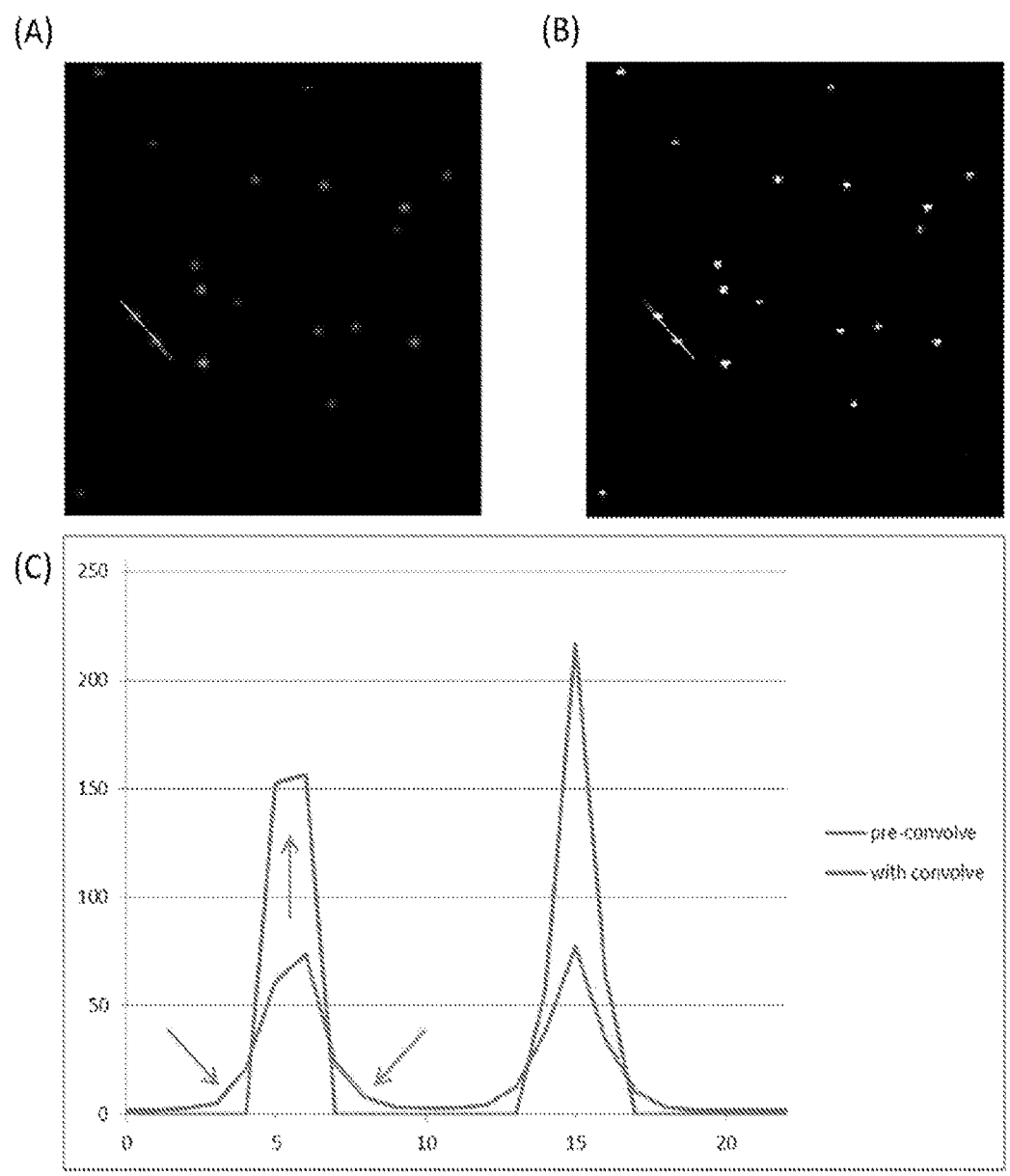
FIG. 6: Effect of Convolve function on an image of QDs. The same image is shown before (A) and after (B) applying the Convolve tool. (C): The intensity profile along a line drawn through two QDs (yellow line in images A and B). Note the sharpening of the particle edge as well as the increase in maximum intensity.

The merged image is converted to an 8-bit grayscale image, preserving the overall intensity of each pixel but removing the color information. Next the Convolve tool is applied to enhance particle uniformity and further improve the signal/background in the image. This spatial convolution function works by multiplying a pixel and its neighbors by a kernel matrix [−1, −1, −11−1, 8, −11−1, −1, −1] and adding the results to calculate a new value for each pixel. The result is that pixels in and at the edges of bright particles are increased and pixels surrounded by low-level background are decreased. FIG. 6 shows an image before and after applying the Convolve function, as well as a profile plot of a line traced across three QD particles. This convolution helps to separate signal from background and aids detection of particles in the image.

Threshold and Particle Counting

ImageJ has built-in functions Threshold and Analyze Particles to automatically determine the number of particles in the image. A particle is defined here as an object of a specified number of contiguous pixels above a certain intensity value. However, because of the inherent variation in QD size, brightness and blinking behavior, the particles present in the images have varying sizes and brightness. To account for this variation and for variability between different images I developed an algorithm for finding the optimal threshold level to maximize the amount of the image background excluded and the number of particles detected. In each image the particle size limit is set to count particles of size between 2 and 12 pixels. The expected size of a single QD was determined by the point-spread function to be 3×3 pixels, but this range allows for some variation in the QD population and defects in the images.

Figure 7:
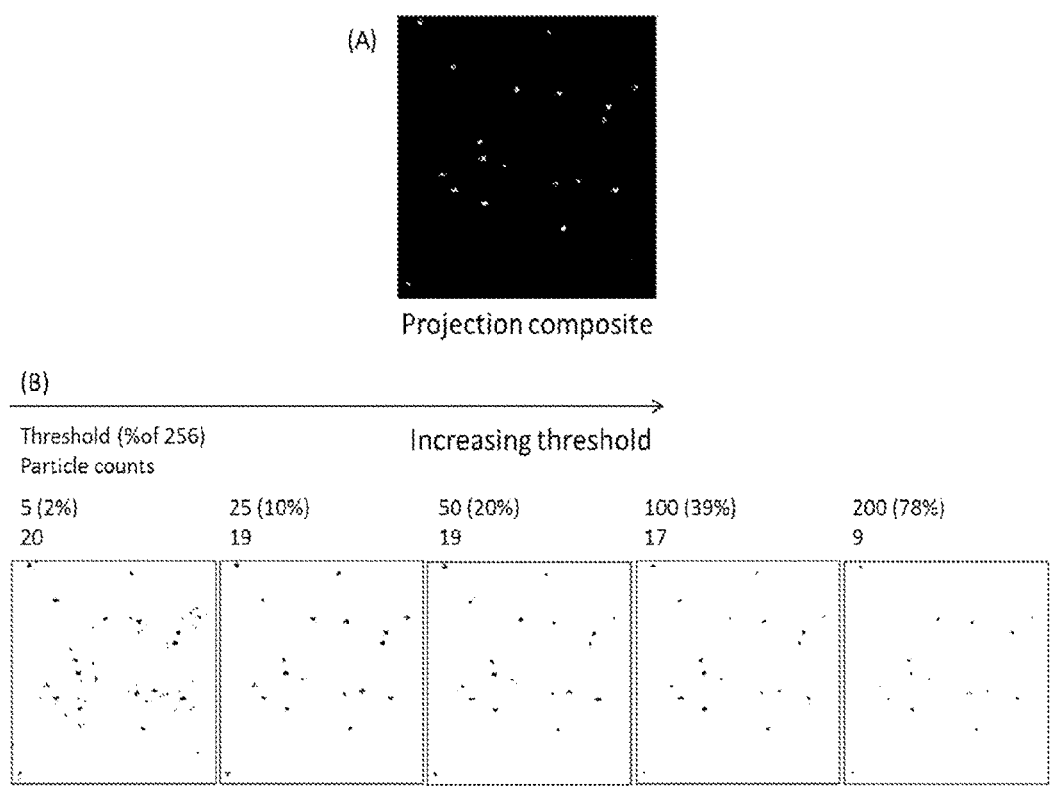
FIG. 7: Increasing threshold yields lower particle count. (A): The same image sub-region used in FIG. 6, after the convolver has been applied. (B): As the applied threshold is increased, fewer particles are counted for the size range 2-12 pixels$^2$.

In a given image and for a certain particle size restriction, the number of particles counted depends on the threshold for several reasons. First, as the threshold is raised some particles will no longer contain enough pixels above the threshold to be counted as a particle (at least 3 pixels needed). At very low threshold, the image background can contribute significantly and cause an unrealistically high number of particles to be counted due to patches of background above the threshold. In the limit as the threshold approaches zero the particle count decreases to zero as well, as very large patches or eventually the entire image would be counted as an object and will be above the size limit. As the threshold level is gradually increased we can see that fewer and fewer particles will be counted, as shown in FIG. 7.

In each image there will be an optimal threshold level where most of the background pixels are eliminated while most of the QD particles are counted. However, this optimal threshold can vary depending on various characteristics of the image such as overall brightness, background level in the image and QD density and brightness.

Automation of Analysis in ImageJ Macro

Figure 8:
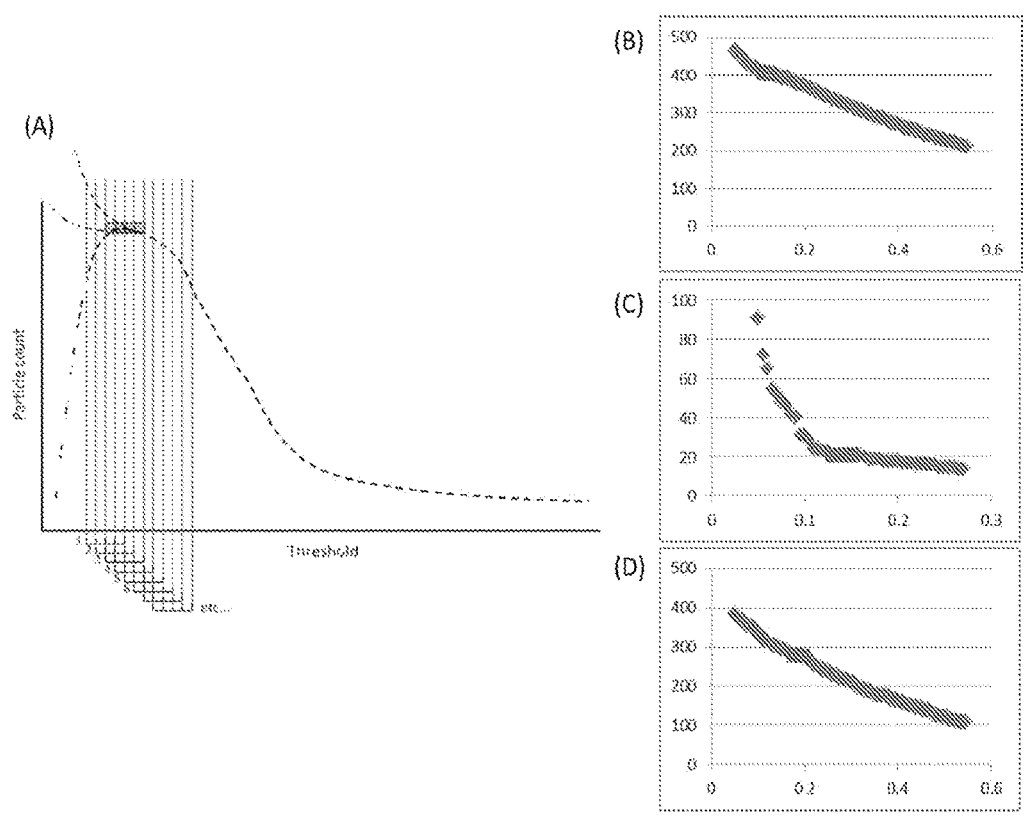
FIG. 8: Particle count vs. threshold behaviors. (A): Sketch of the algorithm selection of optimal threshold range based on the rate of change of particle count with threshold. The curve is exaggerated to illustrate the behavior at the peak or partial plateau. (B)-(D): A variety of behaviors of particle count vs. threshold, taken from data images. The 'optimal' threshold range as selected by the algorithm is highlighted in red for each.

The algorithm determines this optimal threshold for each image based on the set of particle counts across a range of threshold values. The program generates the particle count at incrementally increasing threshold levels over the range from 2% up to 25% or 50% of the image brightness range stepping by 0.5% (the higher threshold values are included in images determined to have high background levels). The algorithm assesses the trend as particle count generally decreases with increasing threshold to select a window where the change in threshold gives the smallest change in particle count, usually a peak or a small plateau in the count as threshold is increasing. FIG. 8 shows the variety of behaviors that can be seen in the dependence of particle count on threshold, and illustrates the binning and window selection used by the algorithm.

Along this particle count vs. threshold curve, every point is addressed as the set of five consecutive steps. The difference between the counts at the first and fifth threshold values is multiplied by the square of the threshold fraction corresponding to the center of the range. This result, termed the 'assessment value' is then compared for every five-step set of threshold intervals. The threshold set with the lowest assessment value is selected as the optimal range. This 'assessment value' is related to the rate of change on the particle count vs. threshold curve over a constant interval size. It is usually also observed that a subset of particles are of very high intensity and so the count vs. threshold curve flattens out in the upper limit (as in FIG. 8), but this is not our desired count range. Multiplying by the square of the threshold fraction of the makes the algorithm more selective for count values in the lower threshold range. This extra preference is justified by comparison of automatic counts with manual counting of images, as this method does give results comparable to a human visual count for the images.

Regardless of the behavior of the count vs. threshold curve at low threshold, there is usually a range where the trend partially flattens or reaches a peak, and so the program assesses an incrementally moving range to find the window with the smallest change. When this optimum range is determined, the algorithm reports the average count value within this threshold range. The width of five steps makes the window a selection of 2.5% of the total range, more flexible than attempting to select a single value but still maintaining accuracy as compared to a human counter.

Results and Discussions

Figure 9:
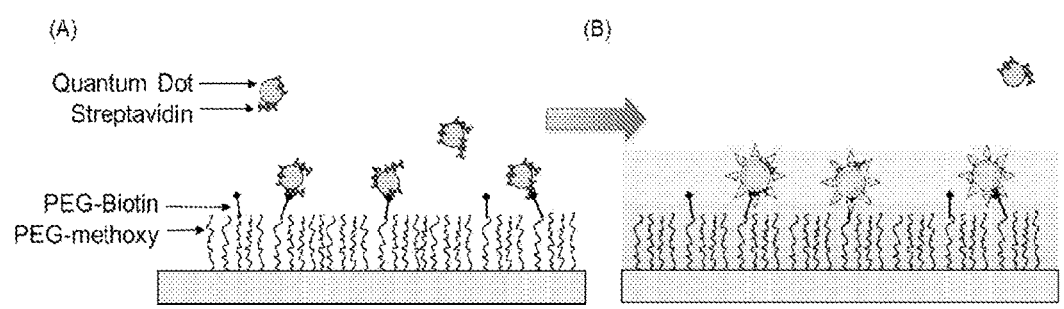
FIG. 9: PEG-biotin+Streptavidin-QDot scheme. SA-QDs in solution will bind to biotin on the PEG monolayer (A). TIRFM enables detection of QDs bound at the surface (B). Note that while some QDs remain in solution (remaining after wash, or due to streptavidin/biotin unbinding), these QDs will be excluded from the excitation and observation volume.

In order to probe and study the signal of individual quantum dots, we first developed a simple assay that takes advantage of the strong affinity of the biotin-streptavidin interaction (FIG. 9). The general strategy was to use Streptavidin-quantum dots (SA-QDs) conjugates and immobilize them onto a biotin-functionalized glass surface to be probed by TIRF illumination. Briefly, the glass surface is modified with an amino-silane followed by addition of a biotin-PEG-succinimidyl valerate (biotin-PEG-SVA), an amine-reactive ester forming a stable amide linkage at the surface. An important advantage here is that the PEG surface is known to reduce nonspecific protein adsorption. An alternative surface preparation method utilized later uses a biotin-PEG-silane reagent, allowing a one-step functionalization.

Figure 10:
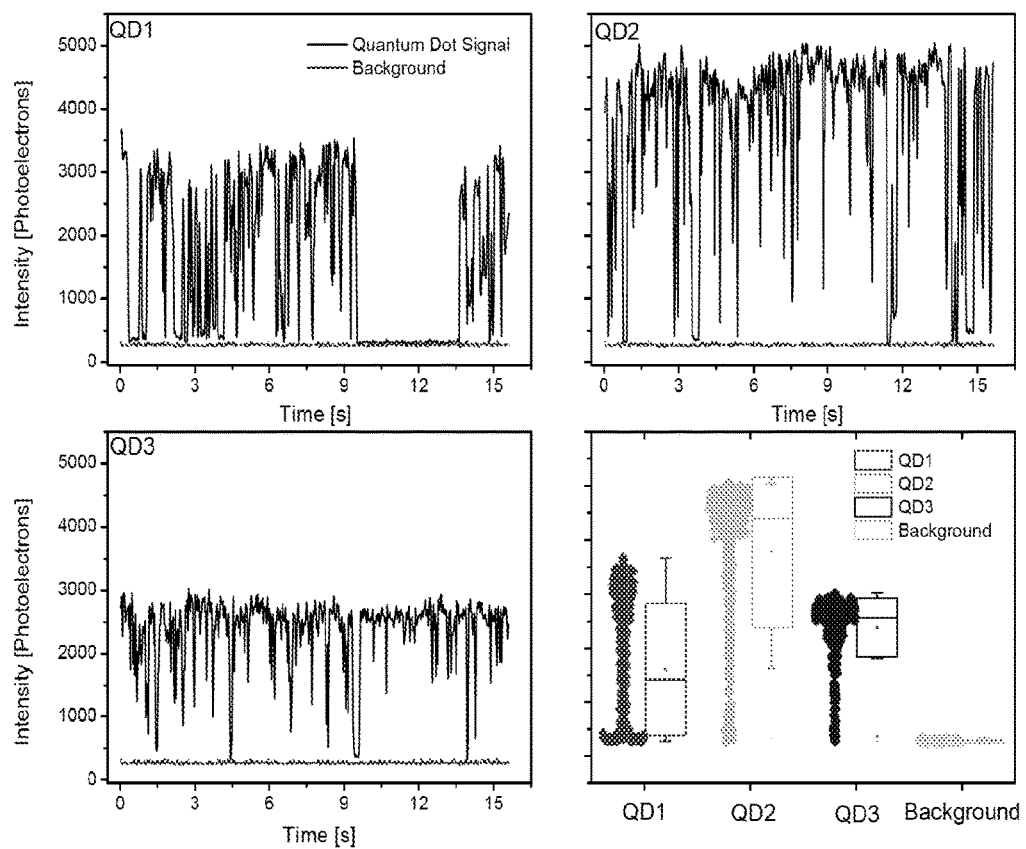
FIG. 10: Signal traces of three different single quantum dots monitored simultaneously. Bottom right: Raw data and boxplot displaying the descriptive statistics of the QD signals: the smallest observation (bottom whisker), standard deviation (box height), median (line in the box), mean (square centered in the box), and largest observation (upper whisker).

FIG. 10 show typical signal traces of single SA-QD conjugates immobilized on a glass surface. A set of QDs will be intrinsically poly-disperse, and the non-uniformities in particle size, shape and composition can contribute to differing observed signal. The examples here display differing maximum brightnesses, frequencies of blinking and extent of off-times. Blinking can result in off-times ranging from many seconds to times shorter than the camera frame rate a range spanning four orders of magnitude. Not only do different QDs display different behaviors but also the same QD can have different behaviors over time. An additional source of variation in the intensity is the physical position of the QD in the sample during TIRF illumination. Due to the exponential decay of the evanescent wave, small differences in the distance from the glass surface can cause significant changes in illumination intensity. Inconsistencies in the sample surface, molecular motions, and different lengths of extension of the PEG surface molecules can all contribute to varying distances within the evanescent wave. The bottom right panel of FIG. 10 shows a box plot of the descriptive statistics of the single QDs signals. It is worth noting that even though QD1 presents higher signal maxima it averages lower signal than QD3 due mainly to an 'off' state for circa 4 sec in the 15 seconds of signal collection, therefore the standard deviation of the from QD1 is higher than QD3.

Considering these behaviors in QD signal intensity, the problem becomes how to reliably detect such an unpredictable signal. The most obvious consideration is to expand the time of the measurement. Under the inverse power-law behavior, as the observation time increases it becomes increasingly unlikely that a QD would have an off-time greater than the observation. Therefore, increasing the observation time increases the probability that fluorescence from any QD in the field of view will be captured. Nevertheless, due to the stochastic nature of the signal longer collection time can still be a problem.

Figure 11:
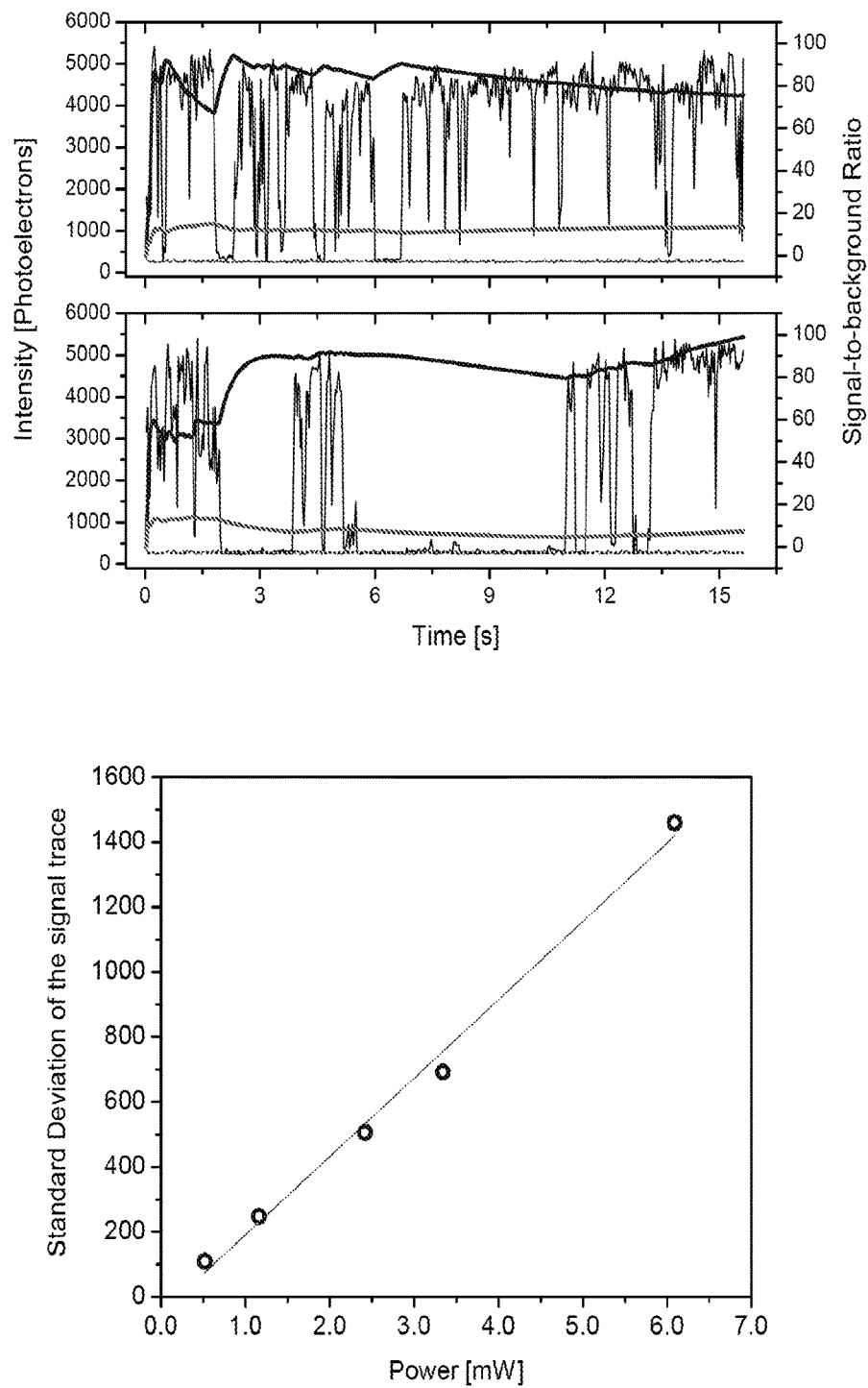
FIG. 11: Top: Signal traces of three different single quantum dots monitored simultaneously. (—) QD signal, (—) background signal, (—) integrated signal-to-background ratio, and (—) standard deviation of the signal to standard deviation of the background ratio. Bottom: Correlation between the laser power at the sample and the standard deviation of a single quantum dots. The signal was recorded over 60 s.

Our way to look at these signals is by probing the variations in the signal as a mean for detection and localization of the QDs. The standard deviation (the variance could also be used) is a measure of the variations or dispersion of data set around its average, therefore the standard deviation could be used to describe the signal of a quantum dot compared to the variations of the background signal. FIG. 11 (Top) compares the progression, in time of the signal-to-background ratios of the integrated signal and the standard deviation of the signal. The two quantum dots display similar emission intensity maxima at the 'on' state (5410 photoelectrons) and they were monitored simultaneously. From the plot is evident that due to the high variations in the QD signal and the small variations in the background signal, the standard deviation of the signal presents a higher contrast ratio between signal and background up to ca 90:1 for the traces in FIG. 11, but typically average ~33:1. The latter compares to the contrast ratio of the integrated signal, which is ca 13:1 in FIG. 11, but averages ~4:1 typically. Thus using the standard deviation as mean for localization of the QD provides a higher contrast and therefore more accurate and reliable detection.

As a corollary using higher excitation power could render higher signal and there for the variability due to the blinking process would also be greater. FIG. 11 (bottom) shows the correlation between the laser power at the sample and standard deviation for the same quantum dot over 60 s of data collection for each point. Interestingly there seem to be a quasi linear correlation between laser power and the standard deviation there for increasing the excitation power can potentially be used to enhance the signal-to-background ratio in the case of the standard deviation and also the signal integration.

Figure 12:
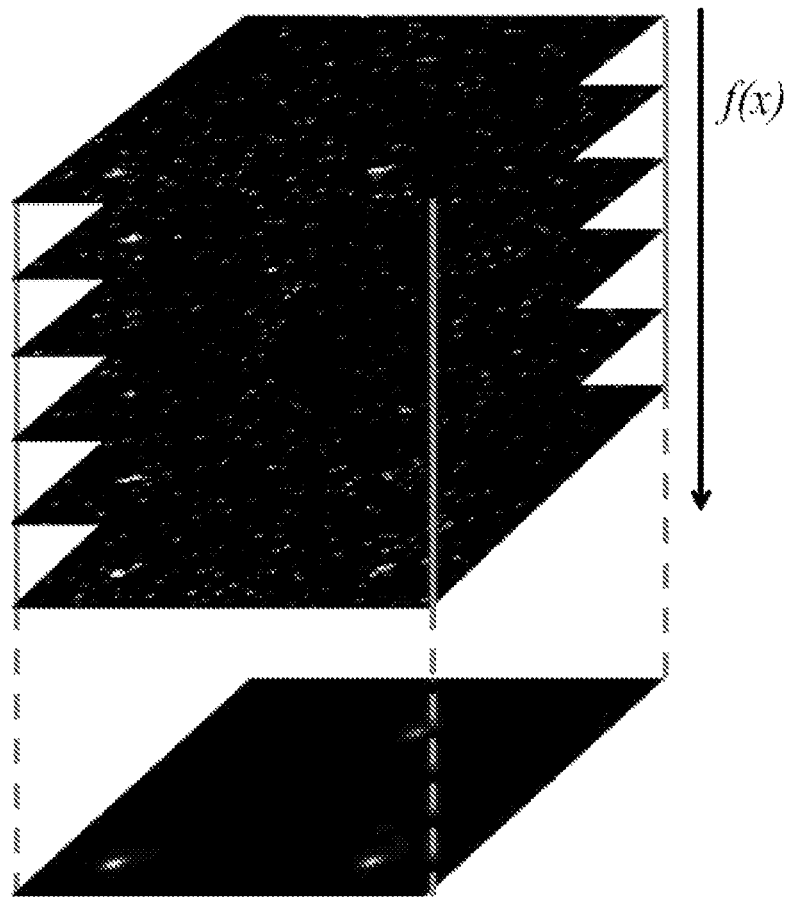
FIG. 12: Projection of an image stack. The movie is a 3-dimensional object, with each x and y in the image plane having a pixel intensity changing over time. Each pixel is treated as a function of time and a mathematical operation is applied, such as the sum

For the quantitative analysis of solutions, it is required that large areas are probed in order to overcome Poisson statistics at very low concentration levels, where the probability of finding a molecule in a given area is close to zero. Therefore, we used total internal reflection fluorescence microscope (TIRFM) imaging that allows for the study of populations of QDs over an area of approximately 100×100 microns at the time. We expected to use a reasonably long observation time ~15 s. For the analysis, image sequences can be converted into a single image using various mathematical functions. This process, called Projecting, takes all the intensity values of a pixel through time and applies some mathematical operation to create a new image based on the result for each pixel over time. The value resulting from the operation applied is then used as the intensity of this pixel in the new projection image, as illustrated in FIG. 12. We can use this image for further processing and analysis to count the individual particles.

Figure 13:
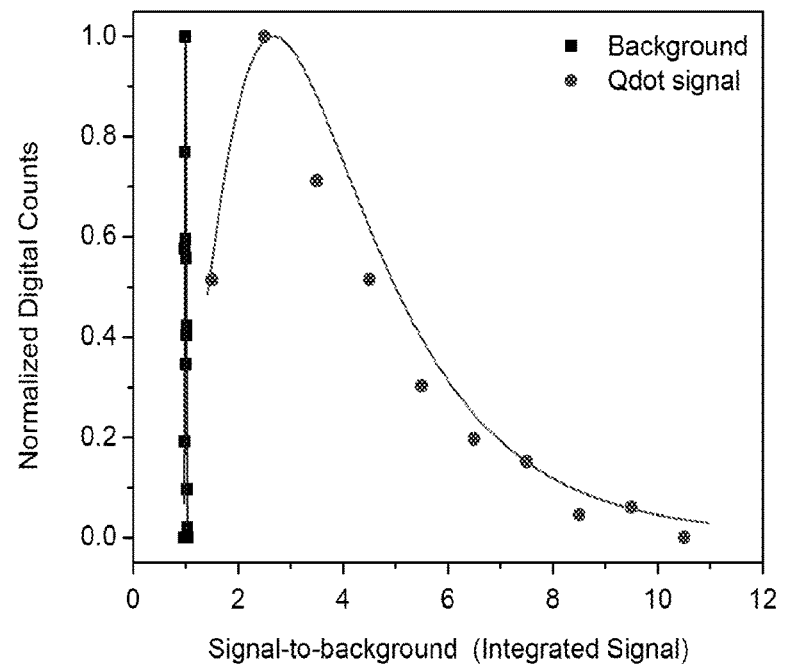
FIG. 13: Normalized histograms of the signal-to-background ratios of the integrated signal (Top) fitted to a lognormal distribution and (Top) and the standard deviation of the signal fitted to a normal distribution (Bottom). In both cases the background signal fits a normal distribution
Figure 13:
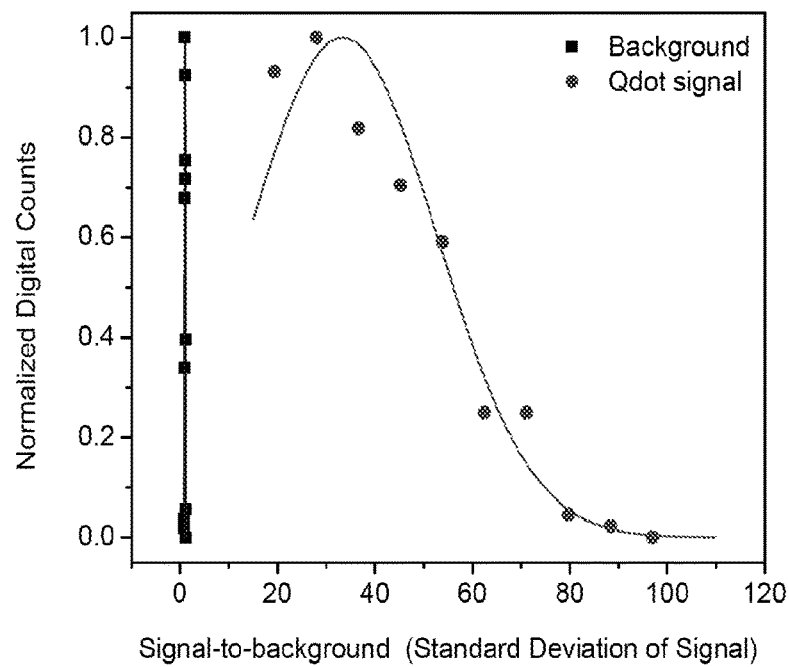

The method of stack integration is a useful solution to capture the integrated and the standard deviation of the signal from populations of QDs over time. FIG. 13 shows the two histograms of the analysis of the QD signals population. After comparing these different projection methods, the Standard Deviation projection provides the best signal-to-background ratio and reveals the presence of QDs which would not be detected using simple integration. Both distributions have similar coefficient of variations (~0.6), thus the improvement of the standard deviation method relies mostly on improvement in the signal-to-background ratio rather than in the tightening of the signals distributions. Incorporating the Standard Deviation into our image analysis improves QD detection by about 10 to 15% compared to simply using the Sum projection. This method addresses the varieties of QD blinking behavior and improves detection using a relatively simple tool for image analysis.

Figure 14:
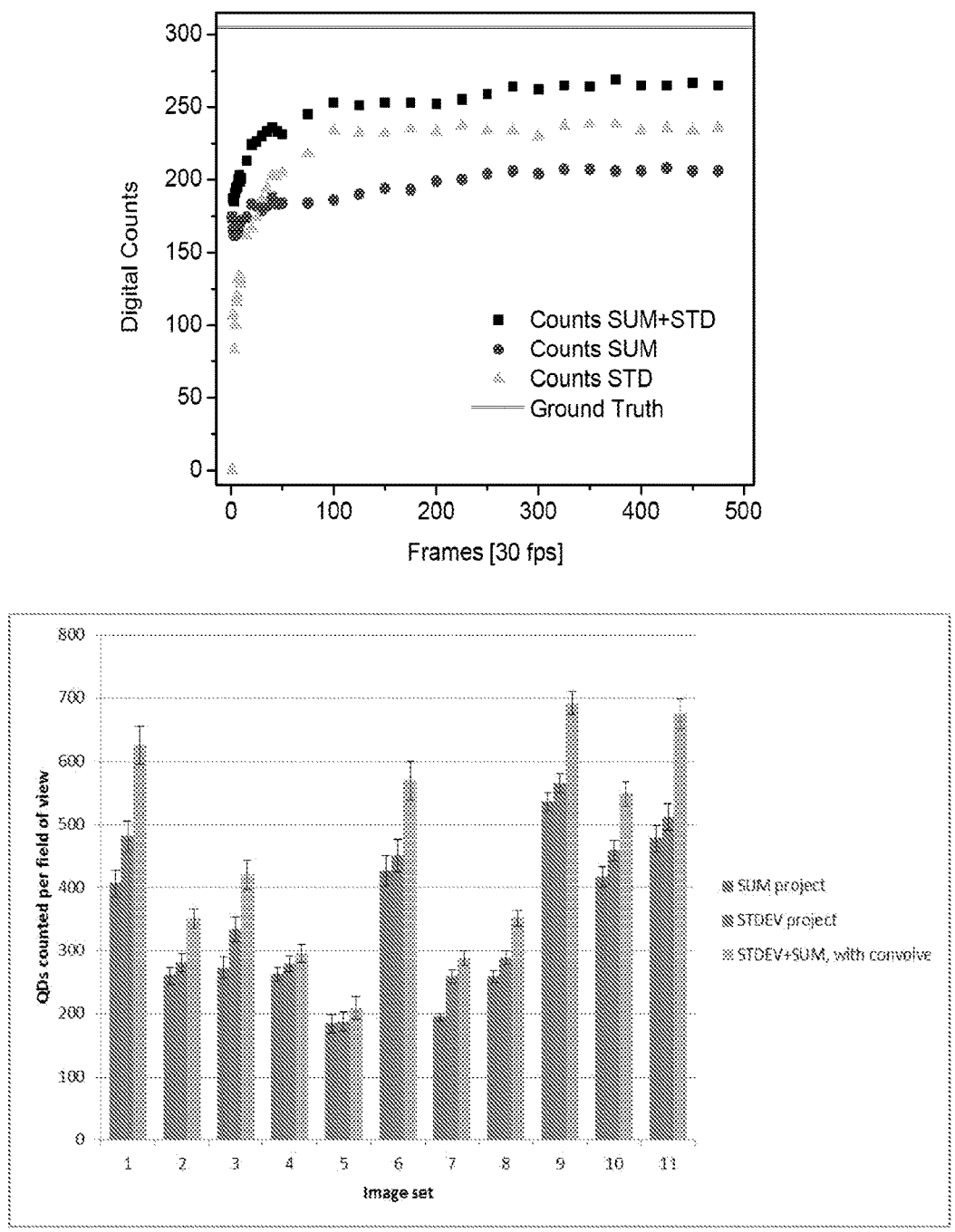
FIG. 14: Top: Digital counts as a function of 'time'. Bottom: Comparison of different projection methods for QD counting. Red: QD counting for the Sum Projection, Blue: the same QD counting methods applied to Standard Deviation Projection. Each image set is seven images taken in the same SA-QD/biotin-PEG sample. Error bars show the standard deviation of the counts over the images in the set. The samples here are taken from various experiments at varying SA-QD concentrations to demonstrate the ability of the Standard Deviation projection over the Sum integration.

Finally, we can envision that there would be quantum dots that could expend most of the observation window in the 'on' state. In that case the standard deviation would be relatively low, but the integrated signal would be high. In order to account for these cases our final methodology incorporates both, Sum and Standard Deviation projection (See experimental section for details). FIG. 14 shows the evolution of the digital counts against the number of images in a sequence collected over a period of time (~15 s). As shown in FIG. 14, the full processing averages 20 to 30% higher QD counts than using only the Sum or Standard Deviation Projections for particle counting analysis. The final method accounts for ca 90% of the ground truth level that was established by the visual inspection of image sequences by analyzing the signal pixel by pixel to ensure that each positive count is derived from a single quantum dots presence.

Figure 15:
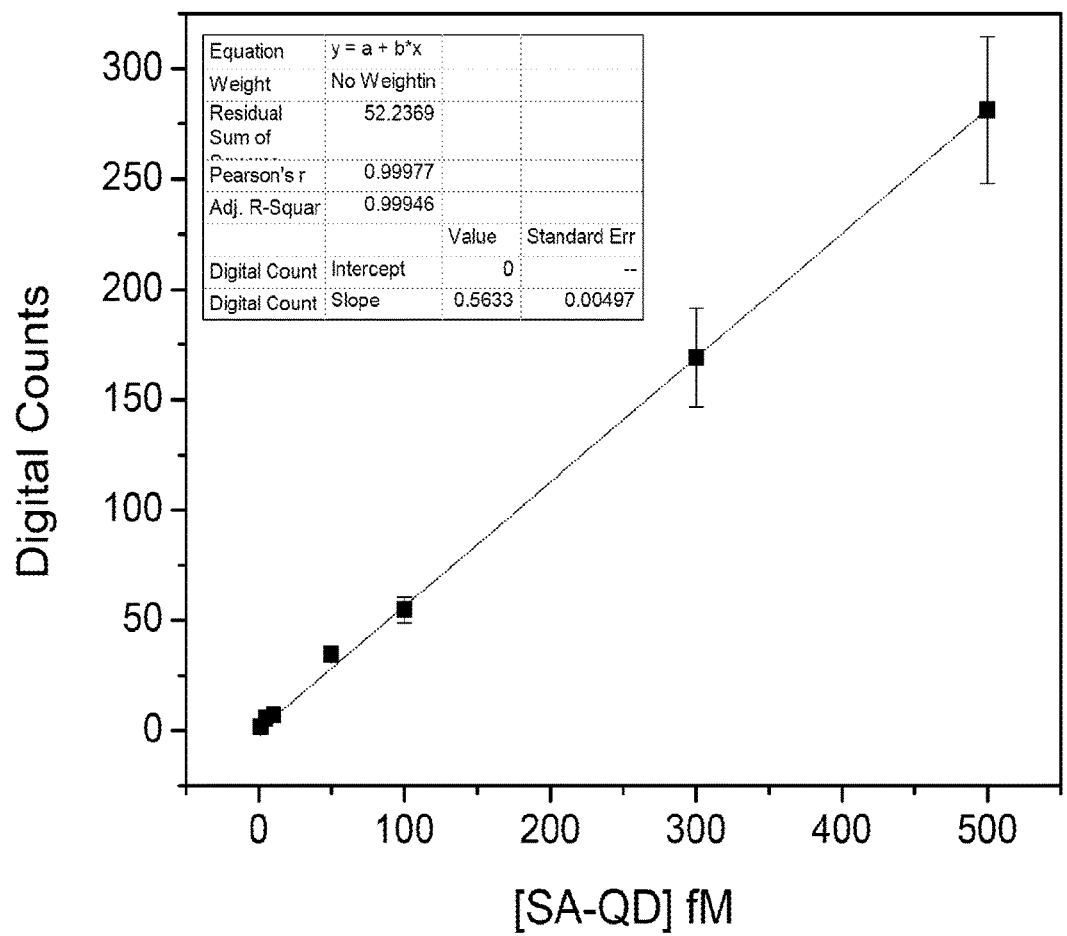
FIG. 15: Calibration curve correlating digital counts of SA-QD on the surface with the concentration of SA-QDs in solution.

After the quantification method was established a calibration curve was measured to correlate digital counts on the probed surface with the concentration of SA-QDs in solution (FIG. 15). The limit-of-detection (LOD) achieved is 1 fM. It is worth noting that this is not an optimized assay and this is proof that our methodology is robust over approximately 3 orders of magnitude. Also, the LOD can be improved by probing larger areas and this could be achieved by scanning the surface. Alternatively, if the biotin functionalize surface is smaller compare to the total volume probed it will concentrate more molecules on the surface at the expenses of incubation time. This could be achieved by combining our detection and analysis methods with a microfluidic platform. In a microfluidic platform the TIRF probing are could be tailored and the complete volume of a sample could be probed in one area of detection. Preliminary experiments have shown a 4-folds increment in sensitivity.

Here we have demonstrated the utilization of a measure of the variation of a signal, standard deviation, to assess stochastic traces of QD reporters. Our method combines integration of the signal over time and calculation of the standard deviation of the signal to yield a robust method of quantification at the single particle level. Our method is rapid, automated and unbiased and it can robustly account for ca 90% of QDs in a field of view. The quantitative methodology developed here for digital quantification of single QDs enables detection at the ~ca sub-femtomolar level, and it is easy suitable for bioanalytical applications for quantification of low levels of DNA.

Other Embodiments and Equivalents

While the present disclosures have been described in conjunction with various embodiments and examples, it is not intended that they be limited to such embodiments or examples. On the contrary, the disclosures encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments, it is to be understood that the disclosure is not restricted to those particular embodiments. Rather, the disclosure includes all embodiments that are functional and/or equivalents of the specific embodiments and features that have been described and illustrated.

We claim:

1. A method comprising:
providing, to a processor of a computing device, data representing level of signal detected at a first time point, $t_1$, from a plurality of locations on a substrate on which at least one single molecule analyte is detectable by virtue of being or being associated with at least one blinking agent, is located at a discrete position;
providing to the processor, data representing level of signal detected at at least one second time point, $t_2$, from the plurality of locations;
processing, by the processor, data sets from each location at each time point, so that a threshold for variation of the level of signal is determined using an algorithm;

based on the determined threshold, establishing that locations with a positive count reflect the presence of the single molecule analyte, whereas other locations do not contain a single molecule analyte and represent background signal.

2. The method of claim 1, wherein the step of processing comprises analyzing, by the processor, the data sets to obtain resulting data selected from the group consisting of standard deviation, sum and combination thereof.

3. A system comprising:
a processor of a computing device;
a storage medium including data detected at at least a first and second time point, $t_1$ and $t_2$, representing level of signal from a plurality of locations on a substrate on which at least one single molecule analyte is detectable by virtue of being or being associated with at least one blinking agent, is located at a discrete position;
memory storing instructions that, when executed, cause the processor to:
process data sets from each location at each time point, so that a threshold for variation of the level of signal is determined using an algorithm;
based on the determined threshold, establish that locations with a positive count reflect the presence of the single molecule analyte, whereas other locations do not contain a single molecule analyte and represent background signal.

* * * * *